United States Patent [19]

Lieberman et al.

[11] Patent Number: 5,223,399
[45] Date of Patent: Jun. 29, 1993

[54] AGRANOLOCYTOSIS SCREENING PROCEDURE

[75] Inventors: Jeffrey A. Lieberman, New York, N.Y.; Edmond J. Yunis, Concord, Mass.

[73] Assignees: Long Island Jewish Medical Center, New Hyde Park, N.Y.; Dana-Farber Cancer Institute, Boston, Mass.

[21] Appl. No.: 671,587

[22] Filed: Mar. 19, 1991

Related U.S. Application Data

[63] Continuation of Ser. No. 521,812, May 10, 1990, abandoned.

[51] Int. Cl.[5] ............................................. G01N 33/53
[52] U.S. Cl. .................................... 435/7.24; 435/975
[58] Field of Search ............................ 435/7.24, 975

[56] References Cited

PUBLICATIONS

A. R. Ahmed et al, *Proc. Natl. Acad. Sci.*, 87, 7658–7662, 1990.

J. A. Lieberman et al, *Arch. Gen. Psychiatry*, 47, 945–948, 1990.

E. L. Milford et al, in B. Dupont (ed.), *Immunobiology of HLA*, vol. I, Springer-Verlag, New York, 1987, pp. 93–106.

*Primary Examiner*—David Saunders
*Attorney, Agent, or Firm*—Robert S. Honor; Melvyn M. Kassenoff; Joseph J. Borovian

[57] ABSTRACT

Certain patients undergoing clozapine drug therapy may be vulnerable to agranulocytosis. It has been found that agranulocytosis vulnerability is correlated with the presence of HLA antigens B38, DR4 and DQw3. Accordingly, a method is provided for detecting such patients, and an HLA kit is provided.

6 Claims, No Drawings

AGRANOLOCYTOSIS SCREENING PROCEDURE

This is a continuation of U.S. patent application Ser. No. 07/521,812, filed May 10, 1990, now abandoned.

This invention relates to a method of screening patients undergoing drug therapy for vulnerability to drug induced agranulocytosis. In particular it relates to a screening procedure to determine before drug therapy is initiated, whether a patient is susceptible to drug induced agranulocytosis.

Agranulocytosis is an infrequent but potentially fatal complication associated with certain drugs, that otherwise have less serious side effects and ordinarily are harmless to most patients. The complication is characterized by leukopenia (white blood count less than 2000/cu.mm.), a total absence of polymorphonuclear leukocytes and relative lymphopenia. If the disorder goes unrecognized and treatment with the drug is not discontinued, agranulocytois will run a progressive course of increasing severity culminating in death from infection. If treatment with the drug is discontinued, complete recovery usually occurs. The period of greatest risk of agranulocytosis developing is in the first 3 to 12 weeks of treatment.

Psychotic drugs such as neuroleptics, trycyclic antidepressants and the benzodiazepines, have been implicated in producing agranulocytosis. The most significant of these is the atypical neuroleptic drug, clozapine, whose chemical name is 8-chloro-11-(4-methyl-1-piperazinyl)-5H-dibenzo[b,e][1,4]diazepine. Clinical studies have shown that clozapine is effective as an antipsychotic agent in patients who are refractory and/or intolerant to classical antipsychotic drug treatment. The compound was found to be superior to standard neuroleptics; and approximately 30% of the patients conservatively defined as being refractory to these neuroleptics significantly improved with clozapine treatment. At the same time, it was found that clozapine does not cause parkinsonism or tardive dyskinesia to the same extent as classical neuroleptics and that it does not elevate prolactin secretion. With regard to tardive dyskinesia, long term treatment with clozapine appears to have a therapeutic effect against this neuroleptic side-effect, particularly the more severe form, tardive dystonia.

Despite its advantages, development of clozapine has been hampered by the apparent increased risk of agranulocytosis. Based on clinical data, the incidence in patients treated for 52 weeks with clozapine is approximately 2%. Because of this risk, patients on a clozapine regimen have to be monitored continually for hematological signs of agranulocytosis onset. A screening procedure which reduced or eliminated the hematological monitoring required in clozapine therapy would be highly desirable in view of the considerable therapeutic potential of clozapine for patients who are unresponsive to or intolerant of the standard neuroleptic drugs.

It has now been found that patients with a vulnerability to agranulocytosis, particularly if they are of Jewish ethnic background, have human leukocyte antigen (HLA) typing which is considerably different than patients who do not develop agranulocytosis. In HLA analysis for A, B, C, DR, and D typing using standard serological procedures, the frequency of the individual B38, DR4 and DQw3 phenotypes in patients who developed agranulocytosis was greater than that for patients who did not develop the disorder. Of much greater significance, the haplotype for the B38, DR4 and DQw3 phenotypes is present in 86.7% of agranulocytosis cases (100% of Jewish agranulocytosis cases) and in only 7.7% of all non-agranulocytosis patients. This is demonstrated by the presence of the B38, DR4 and DQw3 antigens in the agranulocytosis patients. In non-agranulocytois patients, one or more of the three antigens are only rarely present. The instant invention accordingly, provides a method of screening patients for vulnerability to agranulocytosis complications which comprises establishing by HLA analysis the presence of B38, DR4 and DQw3 antigens in said patient. In particular, the invention provides a method of screening patients for agranulocytosis vulnerability, who are about to undergo antipsychotic drug therapy, especially clozapine therapy. The invention also provides a method of establishing the onset of agranulocytosis complications in patients already undergoing drug therapy, especially with antipsychotic drugs, in particular, clozapine.

The instant discovery also makes possible an HLA analysis kit for screening patients for vulnerability to agranulocytosis complications and for the onset of agranulocytosis. Accordingly, this invention further provides an HLA diagnostic kit for use in analyzing for the presence of B38, DR4 and DQw3 antigens in a patient about to undergo or already undergoing drug therapy, in particular anti-psychotic drug therapy, especially clozapine therapy, to determine vulnerability to agranulocytosis complications or the onset of agranulocytosis. The kit provides the reagents and means for detecting B38, DR4 and DQw3 antigens by HLA analysis according to standard serological procedures as described in LABORATORY METHODS IN TRANSPLANTATION IMMUNITY; PROGRESS IN CLINICAL PATHOLOGY 7:239, 1978 and NIH LYMPHOCYTE MICROCYTOTOXICITY TECHNIQUE: NIAID MANUAL OF TISSUE TYPING TECHNIQUE, 1979-1980, NIH, Bethesda, Md.

Following standard serological procedures described in the above references, HLA analysis for phenotypes A, B, C, DR and DQ was performed on 6 patients who had undergone clozapine therapy and had developed agranulocytosis complications. The same analysis was performed on 26 patients, who were undergoing clozapine therapy and had not developed agranulocytosis complications. Four of the agranulocytosis (patient) group and 17 of the non-agranulocytosis (control) groups were male. The average age of the patient group was 30.6 years and the average age of the control group was 27 years. All of the patients were diagnosed as requiring treatment for refractory schizophrenia. Following are the results of the analysis for both groups:

| No. | A | B | Cw | DR | DQw |
|---|---|---|---|---|---|
| PATIENT GROUP | | | | | |
| 1. | 11, 28 | 38, w55 | 3 | 2, 4 | 1, 3 |
| 2. | 3, 26 | 8, 38 | | 3, 4 | 2, 3 |
| 3. | 3, 28 | 8, 38 | | 3, 4 | 2, 3 |
| 4. | 2, 26 | 38 | | 4, 7 | 2, 3 |
| 5. | 3, 24 | 38, 41 | | 4, 5 | 1, 3 |
| 6. | 2X | 37, 44 | 2 | 2, X | 1 |
| CONTROL GROUP | | | | | |
| 1. | 3, 25 | 18, 35 | 4 | | |
| 2. | | | | 2, 5 | 1 |
| 3. | 2, 11 | 44, w52 | | 2, 5 | 1, 3 |
| 4. | 2, 24 | 7, w57 | | 2, 7 | 1, 2 |
| 5. | 2, 28 | 39, 44 | | 4 | 3 |

-continued

| No. | ANTIGEN | | | | |
|---|---|---|---|---|---|
| | A | B | Cw | DR | DQw |
| 6. | 2, 26 | 38, w52 | | 1, 2 | 1 |
| 7. | 2, 24 | 35, w50 | 4 | 3, 5 | 1, 3 |
| 8. | 2, 32 | 44, 51 | 5 | 4 | 3 |
| 9. | 2, 32 | 44, 51 | 5 | 4, 5 | 3 |
| 10. | 2, 30 | 13, 44 | 5 | 4, 7 | 2, 3 |
| 11. | 2, 3 | 38, 50 | | 4, 7 | 2, 3 |
| 12. | 2, 24 | 44, w60 | 2, 3 | 5 | 3 |
| 13. | 2, 26 | 41, w62 | 3 | 1, 5 | 1, 3 |
| 14. | 2 | 18, 35 | 4 | | |
| 15. | 2, 26 | 51, x | | 4, 7 | 2, 3 |
| 16. | 2, 3 | 41, w63 | | 4, 5 | 3 |
| 17. | 3, 28 | 18, 35 | 4 | 1, 4 | 1, 3 |
| 18. | 24, 26 | 13, 38 | | 4, 7 | 2, 3 |
| 19. | 2 | 8, 44 | 5 | 3, 4 | 3 |
| 20. | 2, 24 | 38, 35 | 4 | 2, w6 | 1 |
| 21. | 2, 24 | w50, 40 | | 3, 5 | 2, 3 |
| 22. | 2, 25 | 51, 37 | | 5, w6 | 1, 3 |
| 23. | 23, 26 | 14, 38 | | 1, 5 | 1, 3 |
| 24. | 3, 26 | 50, 35 | | 4, 7 | 2, 3 |
| 25. | 3, 24 | 8, 18 | | 3, 6 | 1, 2 |
| 26. | 2, 3 | 18, 35 | 4 | 1, 4 | 1, 3 |

As can be seen from the above analysis, the B38, DR4 and DQw3 antigen was found in 5 of the 6 patients in the agranulocytosis group, demonstrating that the B38, DR4 and DQw3 haplotype is present in the drug therapy patient who is vulnerable to agranulocytosis complications. In the control group, one or more of the three antigens was not present in any of the patients, with the exception of two patients (both or Jewish ethnic background) both of whom have had limited clozapine exposure and thus may still be at risk. These results demonstrate that the absence of the B38, DR4, DQw3 haplotype is an accurate screening method in determining which drug therapy patients are not vulnerable to agranulocytosis complications.

We claim:

1. A method of screening a patient for vulnerability to agranulocytosis complications from drug therapy which comprises establishing by HLA analysis the presence of B38, DR4 and DQw3 antigens in said patient and relating the presence of said antigens in said patient to a condition of vulnerability to agranulocytosis complications.

2. A method according to claim 1, in which the drug therapy is antipsychotic drug therapy.

3. A method according to claim 1, in which the drug therapy is clozapine therapy.

4. A method of screening a patient undergoing drug therapy for onset of agranulocytosis complications which comprises establishing by HLA analysis the presence of B38, DR4 and DQw3 antigens in said patient and relating the presence of said antigens in said patient to the onset of agranulocytosis complications.

5. A method according to claim 4 in which the patient is undergoing antipsychotic drug therapy.

6. A method according to claim 4, in which the patient is undergoing clozapine therapy.

* * * * *